United States Patent [19]

Rule

[11] 4,239,498

[45] Dec. 16, 1980

[54] METHOD OF PREPARING THYMIC FACTORS AND COMPOSITION

[76] Inventor: Allyn H. Rule, 43 Grove Hill Ave., Newtonville, Mass. 02160

[21] Appl. No.: 963,676

[22] Filed: Nov. 27, 1978

[51] Int. Cl.³ .................... A61K 39/00; A61K 35/12; A61K 37/00; C07G 7/00
[52] U.S. Cl. ...................................... 424/88; 424/95; 424/177; 260/112 R
[58] Field of Search ........................ 424/95, 88, 177; 260/112 R

[56] References Cited

U.S. PATENT DOCUMENTS

| | | | |
|---|---|---|---|
| 3,466,367 | 9/1969 | Jaeger et al. | 424/95 |
| 3,657,417 | 4/1972 | Brunetti et al. | 424/95 |
| 4,010,148 | 3/1977 | Goldstein | 424/177 |
| 4,077,949 | 3/1978 | Goldstein | 424/177 |
| 4,082,737 | 4/1978 | McGregor et al. | 424/177 |
| 4,128,637 | 12/1978 | Naylor et al. | 424/177 |

OTHER PUBLICATIONS

J. of Immunology 117, No. 1, 1976, 313-318.
Khaw, et al., Br. J. Cancer (1973), 28, 288-292.
Miller, et al., Annals New York Academy of Science, pp. 54-60.
Miller, et al., J. of Immunology III, 1973, 1005-1009.
Goldstein, et al., Biochemistry 1966, 1010-1017, vol. 56.
Nathenson, et al., Microbiology 56, 1966, 476-483.
Assaker, et al., "Immunology," 5158.
Theurer-Chem. Abst. vol. 74 (1971), pp. 123, 177y.
Woody et al.,-Chem. Abst., vol. 81 (1974), p. 24043q.

*Primary Examiner*—Delbert R. Phillips

[57] ABSTRACT

A process for obtaining factors having immunological properties from thymus glands including aseptically collecting thymus glands from freshly slaughtered neonatal vertebrates, comminuting the glands in an isotonic aqueous solution, removing fat and solids and heating the resulting solution to sterilize it and precipitate proteins. The solution is then rapidly chilled, and possibly frozen, and subsequently subjected to stage-wise fractionation in a water miscible, nonpolar organic solvent having less than 4 carbon atoms to isolate two factors which have immunological properties, one of which is called a suppressor that represses reconstitution of the immune response and the other of which is called a helper that reconstitutes the immune response.

24 Claims, No Drawings

METHOD OF PREPARING THYMIC FACTORS AND COMPOSITION

BACKGROUND OF THE INVENTION

This invention relates to biological extracts from thymus glands of neo-natal vertebrates and precipitation of factors from these extracts. Particularly, the invention relates to the precipitation of two factors which have immunological properties. One represses reconstitution of the immune response in lethally irradiated thymectomized animals (a suppressor) and the other reconstitutes the immune response (a helper) in such animals and causes in vivo remission of acute monocytic Dunning Leukaemia.

SUMMARY OF THE INVENTION

According to the present invention, thymus glands of neo-natal vertebrates, preferably calves less than about 15 weeks old, are aseptically collected immediately upon slaughter. All connective tissue and fat is removed, and the glands are placed in a cold aqueous solution. The aqueous solutions which I prefer include distilled water, distilled water with physiological buffers such as phosphate or Tris, physiologic saline or equivalent isotonic or substantially isotonic saline solutions. Preferably, the solution is a 0.15 M, Tris-buffered saline at a pH of about 7.2 to 7.4 in a W/V ratio of glands to solution of about 1 to 2 or 4. The glands are then homogenized in a prechilled Waring blender for a few minutes at 4° C. Following, the fat and cellular debris produced during the comminution in the Waring blender is removed by centrifuging the mixture at low speeds, generally between 1500 to 3500 times gravity, for a sufficient time to draw down the solids. The supernatent is then strained through glass wool to remove the solids and a solution is recovered which is then heated to between about 60° to 85° C. for 15 to 30 minutes whereby it is sterilized and proteins are precipitated. The precipitate is removed by low speed centrifugation and the solution is then quickly chilled to less than about 4° C. to prevent the growth of bacteria.

At this point the solution can be frozen for storage which may be a highly desirable break in the work process. If frozen, the subsequent fractionation steps can be effected in that the amount of solvent which is used to precipitate the factors will be changed.

Whether frozen or not, the solution is adjusted to a temperature of about 4° C. and then centrifuged at high speeds, generally in excess of 35,000 times gravity, to precipitate sub-cellular material. The solution is recovered by conventional techniques such as decanting. The supernatent is then ready for a step-wise fractionation, at temperatures less than about 4° C., to separate the previously mentioned factors.

In general, the first step can be admixing the solution with an miscible polar organic solvent having less than four carbon atoms such as methanol, ethanol or preferably acetone to form a mixture having less than 50% by volume solvent and the balance solution and preferably between about 10 and 50% solvent. The solvent extracts the water from some of the material held in the solution and precipitates the factor. I have found that the product of the fractionation step at less than 50% by volume produces a precipitate which contains the immunological suppressor factor.

In order to precipitate the factor containing the immunological helper factor, the previously mentioned solution is further diluted with additional solvent to form a mixture containing greater than 50% by volume solvent and the balance solution and preferably 60 to 75% solvent. Similarly as above, the water is extracted from the materials remaining in the solution and a precipitate will form which contains the helper factor.

While the fractionation above and below 50% by volume separates the helper from the suppressor factor, I have found that a more refined product can be obtained by removing certain materials not relevent to these factors through similar fractionation steps. If the material has not been frozen, the fractionation steps are as follows: The solution from high speed centrifuging is first admixed with the solvent to form a mixture which contains between about 1 and 25% by volume solvent and the balance solution. A precipitate will form at the 1 to 25% dilution, but this material has been found to be substantially immunologically inert for the herein described purposes. The solution resulting after the dilution with 1 to 25% solvent is mixed with additional solvent to form a mixture between about 26 and 50% by volume solvent and the balance solution whereby a second precipitate will form which contains the immunological suppressor factor. Following the recovery of the suppressor factor, the solution can be diluted with additional solvent to form a mixture containing between about 51 to 59% solvent and the balance solution to form a precipitate which again is substantially inert. Then the supernatent is recovered and diluted to between about 60 and 75% by volume solvent and the balance solution to form a precipitate which is recovered and contains the immunological helper factor.

If the solution has been frozen following the high speed centrifugation, it can be mixed with solvent to form a solution which is between about 1 and 10% solvent and the balance solution, at which point a precipitate is formed which is inert for the herein mentioned purposes. The supernatent is then recovered and diluted with additional solvent to form a mixture with between about 11 and 36% solvent and balance solution which precipitates the suppressor factor that is recovered. The solution is then further diluted with additional solvent to form a mixture with between about 37 to 59% solvent and the balance solution, at which point a precipitate is formed which is inert. After removal of the precipitate, the supernatent is further diluted with the solvent to form a mixture with between about 60 to 75% solvent and the balance solution. A precipitate forms which contains the immunological helper factor.

In order to separate the precipitates from supernatents I used decanting or withdrawal by pipette. It is inappropriate, I have found, to use filter paper or glass vessels for the work since the materials in the solution tend to stick and will be removed from the solution without separation.

According to the present invention, I have found that thymic extracts with in vivo activities would cause remission of acute monocytic Dunning Leukaemia in inbred Fisher CD rats if the extract is fractionated into sub fractions to eliminate opposing biologic functions. The data show that certain solvent fractions of calf thymus extracts induce in vitro differentiation of a precurser (suppressor or helper-like) T-cell population of bone marrow origin which go on to express suppressor or helper-like functions in vivo. The suppressor or helper factors also stimulate the appearance of theta antigens on those cells to induce either suppression or helping activities in reconstituting the immune response.

Cells induced in vitro with the helper factor reconstitute the immune response in lethally irradiated thymectomized mice and cause remission of the monocytic Dunning Leukaemia in rats in vivo. Animals in remission rechallenged with Dunning Leukaemic cells at the end of 30 days produced antibodies to the Dunning-specific cell surface antigens instead of dying within 5 to 15 days.

DESCRIPTION OF THE PRIOR ART

In the past, it has been previously disclosed to fractionate, step-wise, extracts from thymic glands. In a paper of Goldstein, Slater and White: Preparation, Assay and Partial Precipitation of Thymic Lymphocytopoietic Factor (Thymosin), Proc. Natn. Acad. Sci, U.S.A.: 56, 1001, it was disclosed to make a single fractionation at 90% solvent dilution. I have found that this dilution was undesirable in that the fraction which was recovered contained both the helper and suppressor factors in varying ratios thereby producing unreliable results when the materials were injected into animals.

Other biologically active extracts of glands have previously been disclosed to the art. The Szent-Gyorgi et al U.S. Pat. No. 3,297,553 relates to a method of extracting and isolating such biologically active materials. The process involved heating the material in organic solvents and acidifying the product. The solution was extracted with chloroform and the chloroform-soluble-fraction was recovered that, in turn, was subjected to chromatographic fractionation to recover active extracts.

The DeSomer et al U.S. Pat. No. 3,438,859 discloses a non-cellular thymus extract which produced activity in immunological situations. The comminuted thymus gland of young calves were suspended in a solution and centrifuged to remove cellular debris. The supernatent was recovered and utilized for its immunological activity. Fractionation, however, is not disclosed by the patent and it would appear that all soluble materials are held in the supernatent.

The Jaeger et al U.S. Pat. No. 3,466,367 also discloses the use of thymus glands for producing an extract, however, the materials are utilized to regulate growth.

In the Japanese Pat. No. 48-11930 owned bythe Teikoku Hormone Manufacturing Company, Ltd., comminuted thymus glands were mixed with an organic solvent followed by drying and then extraction with an aqueous solution of an organic solvent. The solution was dried and the precipitate was recovered, however, no further fractionation of the material is disclosed.

The German patent to Yeda Research and Development Company, Ltd., German Pat. No. 26-28-914 discloses comminuting thymus tissues in neutral solutions and centrifuging the product to remove solvents. The supernatent was dialysed, freeze-dried and then redissolved in a solvent. The solution was filtered with ion exchange resins to produce a material which was disclosed to have immunological properties.

In the Brunetti et al U.S. Pat. No. 3,657,417, a disclosure is made of comminuting large quantities of calf thymus glands and treating them with hydrochloric acid and subsequently sodium hydroxide to obtain an extract. No filtration is disclosed, although the extract is mentioned to be useful in the treatment of leukopenia.

DESCRIPTION OF THE PREFERRED EMBODIMENTS

While not intending to be bound by any mechanism of action, it is believed that the present process acts in accordance with the following examples. The enhancement of immunological competence is demonstrated by the following data which describe, in detail, the processes by which the helper and suppressor factors can be isolated and utilized.

PREPARATION OF THYMIC EXTRACT SUPPRESSOR AND HELPER INDUCING FACTORS

About 2 to 4 kg. thymus glands aseptically obtained from the slaughterhouse are minced following removal of fat and connective tissue. The glands are weighed and placed in sterile cold, (0.01 TRIS-HCl), buffered normal saline, 0.15 N NaCl (1:3 w/v) at pH 7.2 prior to homogenization in a pre-chilled blender 1 to 2 minutes at 0° to 4° C. Aseptic or sterile techniques are followed throughout the whole procedure. The mixture is centrifuged at $2500 \times g$ for 20 minutes and the supernatent that is obtained is strained through glass wool. The precipitate is suspended in an equal volume of the above-mentioned saline and both the supernate and the precipitate (membrane fractions) are heated at 80° C. for 20 minutes. The solids are then precipitated by centrifugation at $2500 \times g$ and the supernatents are decanted. At this point the supernatent may be frozen at $-20°$ to 80° C. After thawing at 4° C. or when preceding without freezing, the extracts are centrifuged at $40,000 \times g$ for 30 minutes at 4° C. The supernatents are then subjected to step-wise acetone fractionation.

(a) Acetone is prechilled to $-20°$ C. and added to the chilled supernatents. A first precipitated fraction is obtained at 10% acetone (v/v) after 30 minutes at 0° to 4° C. with stirring and is discarded. Any precipitate removed at any step is discounted in the volume calculations.

(b) Chilled acetone ($-20°$ C.) is added to bring the volume (solution step a) to 36% acetone. The precipitates obtained after 30 minutes at 0° to 4° C. and centrifugation at $3000 \times g$ are saved, resuspended and solubilized in the buffered saline in the cold and spun at $40,000 \times g$ for 20 minutes.

(c) The supernatents obtained after the 36% acetone fractionation step (b) are diluted to 50% acetone (original volume) for 30 minutes at 0° to 4° C. with stirring, spun at $3000 \times g$ and the supernatent is recovered. The precipitate is suspended in buffered saline for ½ hour with stirring and is then centrifuged at $40,000 \times g$ for 20 minutes.

(d) The supernatents from the 50% acetone fraction (c) are recovered and brought up to 60% acetone (volume/original volume), stirred for 30 minutes at 0° to 4° C. and the precipitate centrifuged out at $3000 \times g$ for 20 minutes. The precipitated product is resuspended and solubilized in the buffered saline while cold (0°–4° C.) with stirring. Immediately thereafter the suspension is centrifuged at $40,000 \times g$ for 20 minutes. The supernatents are recovered.

(e) The supernatents from the 60% acetone fractionation step (d) are then brought up to 75% acetone (volume/original volume), stirred for 30 minutes at 0° to 4° C. and the precipitate centrifuged out at $3000 \times g$ for 20 minutes. The precipitate is resuspended in the buffered saline in the cold at 0° to 4° C. with stirring and spun at 40,000×g and the precipitates and the supernatents are recovered.

(f) The supernatent of the 75% acetone precipitation cut (e) is brought to 90% volume/original volume, chilled to 0° to 4° for 30 minutes and spun at 3000×g for 20 minutes to remove the precipitate. The supernatent is then discarded. The precipitates are resuspended and solubilized in the buffered saline in the cold at 0° to 4° C. with stirring and then centrifuged at 40,000×g for 20 minutes. The supernatent is frozen.

The precipitates from steps (b) and (e) were tested for protein content and ability to reconstitute or repress the immune response in lethally irradiated thymectomized mice. The precipitates resulting from the other steps were found to be substantially immunologically inert for the herein described purpose.

TESTING THYMIC EXTRACT-SUPPRESSOR AND HELPER FACTORS

A. In Vitro Induction of Reduced Antibody Responses in Lethally Irradiated Thymectomized Mice with Thymic Extracts-Suppressor Factor (T-cells)

It is known that bone marrow and thymus cells can reconstitute the immune response to sheep erythrocytes (SRBC) in lethally irradiated (1000R) thymectomized mice and further that bone marrow and suppressor T-cells in this same system do not reconstitute the immune response in these animals.

In my studies BCF, (C57B1/6XC3H/AnF) female mice from Jackson Laboratories of Bar Harbor Maine were used as syngeneic cell donor and recipients. The activity of herein disclosed suppressor factor was tested by incubating 100 micrograms of the factor protein with $10^7$ mouse bone marrow cells in a conventional culture media, for two hours at 37° C. The cells were washed three times in the culture media and $10^7$ cells were injected intravenously into five to seven thymectomized irradiated (1000R) mice which received $10^9$ SRBC according to methods previously published by Miller, Schmeige and Rule: Production of Functional T-cells after Treatment of Bone Marrow and Thymic-Extract Factor J. Immunol. III (P1005) 1973. Controls consisted of bone marrow cells ($10^7$) treated with 100 micrograms of bovine serum albumin (BSA) in place of my suppressor factor or cells incubated for two hours at 37° C. in the along prior to injection of BSA. Suppressor T-cells were obtained for control purposes by adaptively transferring $10^7$ murine thymus cells of the same strain into thymectomized irradiated (1000R) mice. Spleens were assayed in triplicate for the purpose of antibody forming plaques by the modified Jerne tecnhique described by Miller, Schneige and Rule, supra.

T-suppressor cells and the respective spleen control cells were obtained four to six days after the SRBC injections. Spleens were individually meshed, the cells washed and then passed through glass wool followed by nylon wool columns to obtain an enriched T-cell population. $10^7$ T-cells to be tested for suppressor potential were incubated with $10^7$ bone marrow cells. Additionally, $10^7$ unprimed thymocytes were added to each suppressor assay and $2 \times 10^6$ SRBC were placed in each agar culture to provide antigenic stimulation in the presence of complement to assay antibody producing cells as indicated by clear plaques representing immunologically lysed SRBC. It appears that if antibody producing cells are suppressed, statistically fewer antibody producing cells or plaques are present.

Assays were set up in quadruplicate. Eleven days later hemolytic plaque determinations were read in duplicate for 19S (IgM) (Cappel Laboratories, Downington PA) anti-SRBC responses and two were incubated with rabbit anti-mouse IgG (Cappel Laboratories, Downington, PA) which facilitated development and identification of 7S anti-SRBC plaques.

The in vitro stimulation of bone marrow cells by thymic extracts which enable the in vivo suppression of the immune response as demonstrated by reduction of plaque forming assays in the presence of sheep erythrocytes is shown in Table 1.

TABLE 1

IN VIVO SUPPRESSOR-INDUCING ACTIVITIES OF THYMIC EXTRACT ACETONE FRACTION

| BATCH A | | |
|---|---|---|
| ACETONE FRACTION (PERCENT) | PLAQUE FORMING CELLS | |
| | 19S | 7S |
| 0–25 | 530 ± 101 | 723 ± 304 |
| 25–33 | 347 ± 122 | 125 ± 91 |
| 33–50 | 421 ± 105 | 643 ± 224 |
| 50–60 | 602 ± 123 | 805 ± 300 |
| 60–75 | 481 ± 188 | 901 ± 242 |
| CONTROLS | | |
| T-SUPPRESSOR CELLS | 307 ± 113 | 122 ± 72 |
| BACKGROUND | ND | 583 ± 14 |

| BATCH B | | |
|---|---|---|
| ACETONE FRACTION (PERCENT) | PLAQUE FORMING CELLS | |
| | 19S | 7S |
| 0–25 | 102 ± 8 | 35 ± 15 |
| 25–35 | 290 ± 39 | 69 ± 11 |
| 35–50 | 587 ± 142 | 721 ± 149 |
| 50–60 | 633 ± 109 | 832 ± 136 |
| 60–75 | 521 ± 78 | 1015 ± 253 |
| >75 | 736 ± 107 | 1193 ± 187 |
| CONTROLS | | |
| T-SUPPRESSOR CELLS | 30 ± 10 | 80 ± 9 |
| BACKGROUND | 691 ± 230 | 921 ± 211 |

| BATCH C | | |
|---|---|---|
| ACETONE FRACTION (PERCENT) | PLAQUE FORMING CELLS | |
| | 19S | 7S |
| 0–25 | 1117 ± 162 | 981 ± 240 |
| 25–36 | 203 ± 81 | 72 ± 8 |
| 36–50 | 965 ± 122 | 1521 ± 328 |
| 50–60 | 877 ± 105 | 930 ± 145 |
| 60–75 | 789 ± 213 | 1157 ± 189 |
| CONTROLS | | |
| T-SUPPRESSOR CELLS | 30 ± 10 | 80 ± 9 |
| BACKGROUND | 691 ± 230 | 921 ± 211 |

ND = NOT DETERMINED

I have found that extracts which inhibit the production of 19S and 7S antibody production are always found in acetone fractions under 50% v/v but most particularly in the 25 to 36% acetone cut. These suppressor activities are similar to the T-suppressor cells and significantly different from the background controls or plaque forming cells obtained in the presence of non-suppressive thymus extract-acetone fractions. The IgG responses vary from 4.6 to 13.3 times higher in the background or BSA controls than the IgG plaques found in the thymus extract-suppressor factor induced cultures. Variance in the protein content and the rapidity of fractionation do cause slight variables in the fractionation procedures. I have found that a suppressor factor occurs below 50% acetone fractionation and can be clearly separated from thymic extracts which "help" or augment the immune response.

B. In vitro Induction of Enhanced Antibody Responses in Lethally Irradiated Thymectonmized Mice with Thymic Extract-Helper Factor The ability of each fraction to induce in vitro the in vivo activity of immune reconstitution which I define as the helper-inducing factor is shown in the following: 100 micrograms of protein per ml of the various thymic extract-acetone fractions were incubated in culture media with $10^7$ murine bone marrow cells for two hours at 37° C. The cells were washed three times in the culture media and $10^7$ cells were injected intravenously into 5 to 7 thymectomized-irradiated (1000R) mice which received $10^6$ SRBC as the antigen dose. Additional controls consisted of untreated bone marrow cells, marrow cells preincubated with BSA, or animals which were injected with $10^7$ bone marrow and thymocyte cells. All mice were thymectomized, irradiated (1000R) and injected with $10^6$ SRBC according to the method of Miller, Schmiege and Rule, Supra.

Two days after SRBC injection, spleens from the various groups of animals were obtained and independently assayed. Cells were dispersed and enriched for T-cell populations by passage through glass and nylon wool columns which removes B-cells. Then $10^7$ cells were incubated in an in vitro culture system with $10^7$ bone marrow cells and $2 \times 10^6$ SRBC. Eleven days later hemolytic plaque assays described by Miller, Schmiege and Rule were run in duplicate for each helper assay culture. These were incubated in duplicate for 19S anti-SRBC plaque forming cells.

The in vitro stimulation of bone marrow cells by three batches of thymic extract acetone fractions preceding the in vivo development of functional helper T-cell activities in vivo as demonstrated by subsequent production of plaque forming cells (PFC) in the presence of sheep erythrocytes is shown in Table 2. Only the 60 to 75% acetone fraction of these thymic extracts provided significant T-cell help which enabled the reconstruction of the immune response to SRBC. Bone marrow cells treated with helper-inducing factors produced 3.8 to 15.1 times the 19S antibody plaque forming units than cells treated with BSA or cells treated with inactive thymic extract fractions. Thus, the 60 to 75% acetone cut only contained helper-inducing factors which significantly increased SRBC antibody-producing cells.

TABLE 2

ENHANCEMENT OF PLAQUE FORMING CELL (PFC) 19S ACTIVITIES WITH THYMIC EXTRACT HELPER FACTOR

| THYMIC EXTRACT (Batch A) FRACTION | HELPER FACTOR 19S PFC |
|---|---|
| ACETONE (60-75%) | 609 ± 173 |
| ALL OTHERS | 159 ± 83 |
| UNTREATED MC | 47 ± 13 |
| HELPER THYMOCYTE CONTROLS | 532 ± 144 |
| THYMIC EXTRACT (Batch B) FRACTION | HELPER FACTOR 19S PFC |
| ACETONE (60-75%) | 570.5 ± 211 |
| ALL OTHERS | 93.8 ± 92 |
| BSA | 79 ± 15 |
| HELPER THYMOCYTE CONTROL | 684 ± 213 |
| THYMIC EXTRACT (Batch C) FRACTION | HELPER FACTOR 19S PFC |
| ACETONE (60-75%) | 937 ± 213 |
| ALL OTHERS | 68.2 ± 8 |

TABLE 2-continued

ENHANCEMENT OF PLAQUE FORMING CELL (PFC) 19S ACTIVITIES WITH THYMIC EXTRACT HELPER FACTOR

| BSA | 62 ± 9 |
|---|---|
| HELPER THYMOCYTE CONTROL | 1008 ± 162 |

C. Anti-Leukaemic Activities of Thymic-Suppressor and Helper Inducing Factors Previous studies by Khaw and Rule, Immunotherapy of the Dunning Leukaemia with Thymic Extracts Br. J. Cancer 28:228 (1973) had shown that certain batches of crude thymic extract were able to cause remission of the acute monocytic Dunning Leukaemia passaged as an ascites tumor in Fisher CD rats. Moreover, many of the batches which didn't work in this system would not reconstitute the immune response to SRBC either. See Miller, Schmiege and Rule Supra.

Dunning Leukaemia cells ($10^4$) were washed three times in saline at 800 RPM, incubated in hypotonic saline at 37° C. or 4° C. for two hours, washed, centrifuged and injected IV into Fisher-CD rats. At this point in time (passage 102) the saline treatment did not affect viability but did allow rats to live an additional 2 to 3 days with the same innoculum. The helper inducing factor or suppressor-inducing factor of this invention was administered intravenously (2 mg/ml) on days $-3$ to $-1$ prior to and on days $+1$ to $+3$ after tumor injection. Unseparated, crude thymic extract (5 mg/ml) was injected in the same dosage schedule. A total of 10 rats per group of 40 rats were sub-divided into similar groups and treated the same way except that the tumor cells were inject in 1 ml ascites fluid. In another group of 10 rats, cells pretreated in hypotonic saline were allowed to sit one hour in 2 mg/ml of my helper inducing factor (TE-HIF) or 2 mg/ml of TE-suppressor inducing factor (TE-ISF) at room temperature and injected in the presence of either the TE-HIF or TE-SIF respectively. After all treatments, viability was checked and remained greater than 94%.

In rats undergoing remission of the Dunning Leukaemia, after 30 days, I repeated injections of $10^5$ leukaemic cells every 7 days. Such injections did not reintroduce the leukaemic state, but produced syngeneic antibodies after three injections with agglutinating titers of 1:128. (Control animals died in 5 to 6 days). Then 0.25 ml of these antibodies were introduced at days $+5$, $+10$ and $+15$ after the injection of $10^4$ Dunning cells to previously unchallenged rats to obtain remission.

At the 102nd passage of the Dunning Leukaemia, my helper factor could induce remission of the Dunning Leukaemia only when incubated with the leukaemic cells and injected with 2 mg of the thymic extract-helper inducing factor. At this passage mean survival time of untreated cells was nine days and preincubation in 0.7% saline at 37° C. allowed 12 days of survival time. At this point, neither thymic extract helper factor nor suppressor factor could induce remission or increase the mean survival time from the saline control although injection of the crude extract did prolong survival time an additional 3.7 days. Preincubation of the Dunning cells in 2 mg of thymic extract-suppressor factor protein increased survival time by four days and induced a remission in one rat. Injection of saline treated cells in 1 ml of the ascites fluid decreased the mean survival time to that of the untreated cell controls (9 days). The ascites were tested in the suppressor assay systems but could not suppress PFC compared with TE-SIF treated bone marrow or suppressor T-cell controls.

With an additional 8 passages of the Dunning Leukaemia occurring during this experiment interval, a mean survival time of 9 to 10 days after passage was obtained in rats receiving $10^4$ days. With this shortened survival time, an appropriate immune response could not be obtained by any mode of administration of the thymic extract or the helper or the supressor factor. However, from the 142nd to the 200th passage, administration of 0.25 ml of syngeneic antibodies to Dunning Leukaemia cells at days +5, +10 and +15 could induce total remissions in rats receiving $10^4$ Dunning cells incubated in hypotonic saline leukaemia cells. At the 142nd passage over 80% of the Dunning cells were in division.

D. Anti-Leukaemic Activities of Helper-Inducing Factors Following BCNU Chemotherapy As the Dunning Leukaemia in the inbred Fisher CD rats became more virulent, i.e. $10^3$ cells now killing animals in 5 to 6 days, an immunotherapeutic agent no longer had time to promote tumor rejection. I thus chose the anti-leukaemic agent, BCNU, carmustine or bichloronitrosourea to prolong survival time prior to the use of thymic extract-helper and suppressor factors to attempt to prolong survival or promote total remission.

BCNU dosages (mg/kg) were chosen at levels currently used to treat leukaemia. At 26.6 mg/kg pulsed 1 day following the passage of the tumor, mean survival time was prolonged from an average of 26 days (15 to 36 days actual). Thus, immunotherapy with thymic extract factors was initiated at day +10 (intravenously) when BCNU treatment was controlling the cancer but white blood cells had increased 10%. Results of these experiments are found in Table 3.

Administration of $10^3$ Dunning leukaemia cells to control animals caused death within six days; those additionally treated at day +1 with BCNU had a mean survival time of 26 days +11/−10 but no animals went into remission. Animals given $10^3$ Dunning cells at day 0, 26.6 mg/kg of BCNU at day +1, and 2 mg of helper-inducing thymic extract given intravenously to each rat at day +10 had a mean survival time of 30.1 days; additionally 16% were in remission at day 52. Rats in remission did not die with a rechallenge of $10^5$ cells. If syngeneic antibodies to the Dunning Leukaemia were administered at day +10 after passage and BCNU treatment at day +1 significant survival could also be obtained. The final experiment at day 75 is shown in Table 4. If BCNU were not administered but antibodies were injected at day +3, +8 and +13 after receiving the Dunning Leukaemia, 100% went into remission.

These data show that both thymic extract helper factors and antibodies produced by animals undergoing remission by the previous modality protect animals against death caused by the Dunning Leukaemia.

TABLE 3

MEAN SURVIVAL TIME OF LEUKAEMIC FISHER CD RATS RECEIVING THYMIC EXTRACTS OR SYNGENEIC ANTIBODY AFTER BCNU - TREATMENT

| NUMBER OF RATS | TREATMENT (IV) BCNU (mg/kg) | Thymic Extract (TE) (mg. protein) | MST (days) | % REMISSION |
|---|---|---|---|---|
| 1. 10 | — | — | 6 | 0 |
| 2. 19 | Day +1(26.6) | — | 26 | 0 |
| 3. 19 | Day +1(26.6) | Day +10 "Helper" TE 2 mg. | 30.1 | 16 |
| 4. 15 | Day +1(26.6) | Day +10 Antibody** | 28.5 | 45 |
| 5. 15 | — | Day +3, +8, +13 Antibody** | — | 100 |

These experiments reflect ongoing experiments at day 52 after injection of the Dunning Leukaemia.
**Antibodies were obtained in animals which survived after previous "helper" treatment; titer 1/128 by agglutination titration.

TABLE 4

MEAN SURVIVAL TIME OF LEUKAEMIC FISCHER CD RATS RECEIVING THYMIC EXTRACTS OR SYNGENEIC ANTIBODY AFTER BCNU TREATMENT

| Group | # Rats | BCNU mg/kg | Thymic extract mg protein | MST | % Remission |
|---|---|---|---|---|---|
| 1 | 20 | — | — | 6 | 0 |
| 2 | 23 | day +1 = 26.6 mg/kg I.v | — | 25.54 | 0 |
| 3 | 20 | day +1 = 26.6 mg/kg | day +10 crude T.E. 5 mg | 25.37 | 0 |
| 4 | 20 | day +1 = 26.6 mg/kg | day +10 "suppressor" T.E. 2 mg | 19.45 | 0 |
| 5 | 24 | day +1 = 26.6 mg/kg | day +10 "helper" T.E. 2 mg. | 32.7 | 0 |
| 6 | 20 | day +1 = 26.6 mg/kg | day +10 Antibody** | 46.42 | 0 |
| 7 | 15 | — | day +3, +8, +13 Antibody** | — | 100 |

These experiments reflect ongoing experiments at day 97 days after injection of the Dunning leukaemia.
**Antibodies were obtained in animals which survived after previous "helper" treatment; titer by agglutination titration.

It is apparent that modifications and changes can be made within the spirit and scope of the present invention. But it is my intention, however, only to be limited by the appended claims.

I claim:

1. A process for recovering fractions having immunological properties, the steps which comprise:
  collecting thymus glands of neo-natal vertebrates aseptically upon slaughter and removing fat and connective tissue;
  comminuting said glands in a cold aqueous solution;
  removing fat and cellular debris produced during the comminution and recovering a solution;
  heating said solution to between 60° and 85° C. whereby the solution is sterilized and proteins are precipitated;
  rapidly chilling the solution to less than about 4° C., removing the precipitate and recovering the solution;
  precipitating sub-cellular material and recovering the solution;
  admixing the solution with a water miscible organic non-polar solvent to form a mixture with between about 10 and 50% by volume solvent and the balance solution, whereby a precipitate will form, and recovering the precipitate which contains an immunological suppressor factor.

2. An immunological suppressor factor prepared according to the process of claim 1.

3. The process according to claim 1 wherein the aqueous solution is isotonic saline.

4. The process according to claim 1 further including the step of admixing the solution remaining after removal of the precipitate containing the immunological suppressor factor with additional water miscible, organic non-polar solvent to form a mixture with between about 51 and 90% by volume solvent and the balance solution, whereby a precipitate will form and recovering the precipitate which contains an immunological helper factor.

5. An immunological helper factor prepared according to the process of claim 4.

6. The process according to claim 1 further including continuing the step of the rapid chilling to less than about 4° C. to freeze the solution and then thawing the solution and removing the precipitate from the solution and recovering the solution as aforesaid.

7. The process according to claim 1 wherein after precipitating sub-cellular material, the recovered solution is admixed with said solvent to form a mixture of between about 1 and 10% by volume solvent and the balance solution, whereby a precipitate will form, removing the precipitate and then admixing the solution with additional solvent to form a mixture with between about 26 and 50% by volume solvent and the balance solution, whereby precipitate will form which contains said immunological suppressor factor.

8. The process according to claim 1 further including the step of admixing the solution remaining after removal of the precipitate containing the immunological suppressor factor with additional solvent to form a mixture containing between about 60 and 75% by volume solvent and the balance solution, whereby a precipitate will form and recovering the precipitate which contains an immunological helper factor.

9. The process according to claim 8 wherein prior to admixing the solution to form a mixture containing 60 to 75% by volume solvent, the solution is admixed to form a solution containing between about 51 to 59% by volume precipitate which is inert and recovering the solution for further dilution.

10. The process according to claim 1 wherein the sub-cellular material is precipitated by high speed centrifugation at speeds above about 35,000×G.

11. The process according to claim 1 wherein the solvent is a member selected from the group consisting of methanol, ethanol and acetone.

12. The process according to claim 8 wherein the thymus glands are removed from calves.

13. The process according to claim 1 wherein the solution which is heated to between about 60° and 85° C. is maintained at that temperature for 15 to 30 minutes.

14. A process for removing fractions having immunological properties, the steps which comprise:
collecting thymus glands of neo-natal vertebrates aseptically upon slaughter and removing fat and connective tissue;
comminuting said glands in an aqueous solution;
removing fat and cellular debris produced during the comminution and recovering the solution;
heating said solution to between about 60° and 85° C. whereby the solution is sterilized and proteins are precipitated;
rapidly chilling the solution to less than 4° C. and removing said precipitate from the solution and then freezing the solution;
thawing said solution to temperatures less than about 4° C. and precipitating sub-cellular matter and recovering the solution;
admixing the solution with a water miscible organic non-polar solvent to form a mixture with between about 1 and 36% solvent and the balance solution, whereby a precipitate will form and recovering the precipitate which contains an immunological suppressor factor.

15. The immunological suppressor factor prepared according to the process of claim 14.

16. The process according to claim 14 wherein the aqueous solution is isotonic saline.

17. The process according to claim 14 further including the step of recovering the the solution remaining after removing the precipitate containing the immunological suppressor factor and admixing said solution with additional quantities of said member to form a mixture containing between about 60 to 75% by volume of said member and the balance solution, whereby a precipitate will form and then recovering the precipitate which contains an immunological helper factor.

18. The process according to claim 17 wherein prior to admixing the solution to form a mixture containing 60 to 75% by volume solvent, the solution is admixed to form a solution containing between about 51 to 59% by volume precipitate which is inert and recovering the solution for further dilution.

19. The process according to claim 14 wherein the thymus glands are removed from calves.

20. The process according to claim 14 wherein the solution which is heated to between 60° and 85° C. is maintained at that temperature for 15 to 30 minutes.

21. The process according to claim 14 wherein after precipitating sub-cellular material the solution is admixed with the water miscible non-polar solvent to form a mixture between about 1 and 10% solvent and the balance solution, whereby a precipitate will form that is immunologically inert.

22. The process according to claim 17 wherein prior to forming the solution containing 60 to 75% solvent, the solution is admixed with solvent to form a mixture between about 37 to 59% by volume solvent and the balance solution, whereby a precipitate will form that is immunologically inert.

23. The process according to claim 14 wherein the solvent is selected from the group consisting of methanol, ethanol and acetone.

24. The process according to claim 14 wherein the sub-cellular material is precipitated by high speed centrifugation at speeds above about 35,000×G.

* * * * *